(12) United States Patent
Eijck

(10) Patent No.: US 7,727,008 B1
(45) Date of Patent: Jun. 1, 2010

(54) ELECTRICAL CONNECTOR FOR CONVEYING AN ELECTRICAL SIGNAL FROM A DEVICE TO AN ORGAN OF A HUMAN OR ANIMAL BODY

(75) Inventor: Rogier Eric Emile Eijck, Roermond (NL)

(73) Assignee: European Custom Manufacturing B.V., Gemert (NL)

( * ) Notice: Subject to any disclaimer, the term of this patent is extended or adjusted under 35 U.S.C. 154(b) by 0 days.

(21) Appl. No.: 12/397,716

(22) Filed: Mar. 4, 2009

(51) Int. Cl.
*H01R 11/00* (2006.01)
*A61N 1/375* (2006.01)
(52) U.S. Cl. .......................... 439/505; 439/909; 607/37
(58) Field of Classification Search ................. 439/505, 439/909; 607/37
See application file for complete search history.

(56) References Cited

U.S. PATENT DOCUMENTS

| | | | | |
|---|---|---|---|---|
| 4,685,467 A | * | 8/1987 | Cartmell et al. | 439/909 |
| 6,032,063 A | * | 2/2000 | Hoar et al. | 439/909 |
| 6,254,425 B1 | * | 7/2001 | Shchervinsky et al. | 439/502 |
| 7,241,180 B1 | * | 7/2007 | Rentas Torres | 439/909 |
| 2002/0198522 A1 | * | 12/2002 | Kordis | 607/122 |
| 2003/0004505 A1 | * | 1/2003 | Bencini et al. | 607/101 |

* cited by examiner

*Primary Examiner*—Briggitte R Hammond
(74) *Attorney, Agent, or Firm*—The Webb Law Firm

(57) ABSTRACT

The invention relates to an electrical connector for conveying an electrical signal from a device, in particular a cardiac device, to an organ of a human or animal body, in particular a heart, comprising a first electrically conducting wire and a second electrically conducting wire, wherein the wires are joined together in an electrically insulating sleeve, a first electrode, which is electrically connected to the first wire, and a second electrode, which is electrically connected to the second wire; wherein the first and second electrodes are constructed to deliver an electrical signal at the organ, wherein the first electrode forms an electrically conducting sleeve around a conducting part of the first wire and around a non-conducting part of the second wire, wherein at least the edges of the electrically conducting sleeve formed by the first electrode are at least partially embedded in the electrically insulating sleeve.

15 Claims, 3 Drawing Sheets

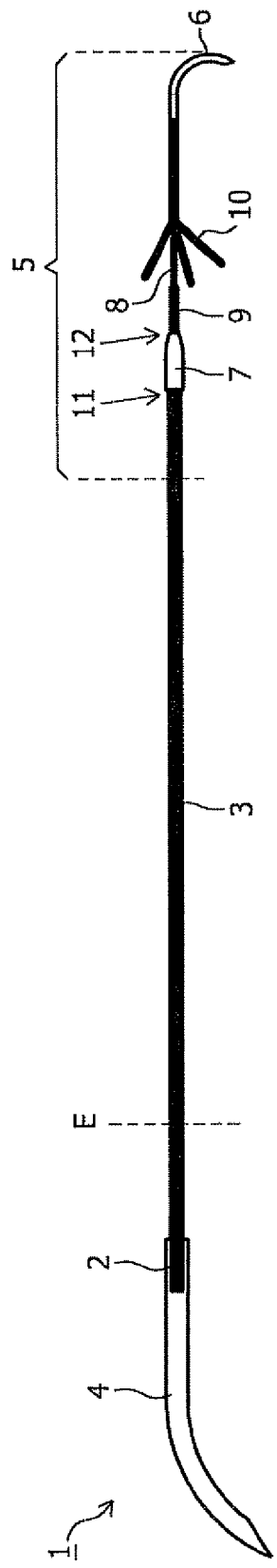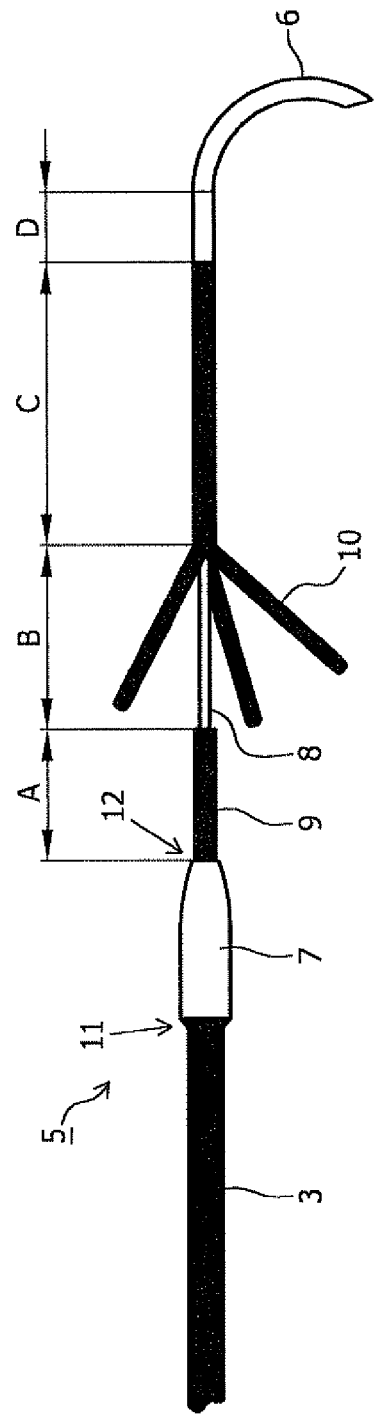

ELECTRICAL CONNECTOR FOR CONVEYING AN ELECTRICAL SIGNAL FROM A DEVICE TO AN ORGAN OF A HUMAN OR ANIMAL BODY

BACKGROUND OF THE INVENTION

The invention relates to an electrical connector for conveying an electrical signal from a device, in particular a cardiac device, to an organ of a human or animal body, in particular a heart for an organ of a human or animal body.

Electrical connectors are increasingly used in the medical field for stimulating organs. A well known application is the stimulation of the heart. Many different connectors exist, that typically comprise a bipolar connector having at least two parallel wires, that are connected to a device generating electrical signals, for example a heart pacemaker, and provided with electrodes attached to the organ to be stimulated on the opposite end of the wire. Usually, the connector is inserted into the body and attached to the organ in a surgical operation. Often, the connector is used temporarily, and may be removed at a later stage by retracting the connector and its electrodes. Both the insertion and retracting operations involve a risk of medical complications in the treated person.

SUMMARY OF THE INVENTION

It is an object of the invention to provide an improved electrical connector for conveying an electrical signal from a device, in particular a cardiac device, to an organ of a human or animal body, in particular a heart.

The invention provides an electrical connector for conveying an electrical signal from a device, in particular a cardiac device, to an organ of a human or animal body, in particular a heart, comprising: at least a first electrically conducting wire and a second electrically conducting wire, wherein the wires are joint together in an electrically insulating sleeve, a first electrode, which is electrically connected to the first wire, and, a second electrode, which is electrically connected to the second wire; wherein the first and second electrodes are constructed to deliver an electrical signal at the organ; wherein the first electrode forms an electrically conducting sleeve around a conducting part of the first wire and around a non-conducting part of the second wire; wherein at least the edges of the electrically conducting sleeve formed by the first electrode are at least partially embedded in the electrically insulating sleeve. The connector according to the invention allows for easier and safer insertion and removal from the organ of human or animal body. As the edges of the electrically conducting sleeve electrode are embedded in the electrically insulating sleeve, the adjoined sleeves form a substantially continuous outer surface. As a result of the obtained smooth surface, the force needed for inserting or retracting the electrical connector are relatively low, and the edges of the electrode do not cut into tissue during movements. Therefore, the chances for damages to body tissue while moving the wire in or out of the body are significantly reduced. This also reduces the chances for complications after surgery, in particular if the electrical connector is used for connecting a pacemaker device to a heart.

The electrically conducting wires are made of electrically conducting materials of a suitable thickness, using suitable materials known in the art. For the electrically insulating sleeve, preferably a physiologically acceptable flexible material is used, which allows for adaptation of its formed when implanted in an animal or person. Such materials are also known in the art. The electrodes have a suitable electrically conducting surface, preferably made out of a metal such as stainless steel, to deliver an electrical signal from for instance a pacemaker at the desired location at a sufficient power level. The first electrode forming an electrically conducting sleeve around a conducting part of the first wire and around a non-conducting part of the second wire may be have a generally cylindrical or cylinder-derived shape. The electrically conducting sleeve does not necessarily form a full enclosure, but may also partially enclose the first and second wires in a clamp-like manner. The electrically conducting sleeve may be essentially rigid but is preferably constructed as a resilient sleeve which may be deformed in order to shape the electrically conducting sleeve. The electrically conducting sleeve formed by the first electrode is at least partially embedded in the electrically insulating sleeve, which may be achieved for instance by having a depression in the isolating sleeve which accommodates at least the edges of the electrically conducting sleeve, or by pressing the edges into the resilient isolating material. Thus, the outer circumference of the edges of the electrically conducting sleeve is equal to or smaller than the adjacent insulating material. The sleeve itself may fur instance be of an essentially cylindrical, conical or curved shape. The distal ends of first and second wires away from the electrodes are suitable for connection to a device, in particular a cardiac device/pacemaker, as in a regular electrical connector for the same purpose.

In a preferred embodiment, the second wire extends through the electrically conducting sleeve formed by the first electrode towards the second electrode. Such construction is relatively easy to prepare and allows for a reliable electrode configuration. Along the length of the connector, the second electrode is located at a predetermined length from the first electrode.

It is advantageous if the electrically conducting sleeve formed by the first electrode is connected to a distal end of the first wire located inside the electrically conducting sleeve. Thus, the first wire terminates at the first electrode, allowing for a reliable connection. Also, this allows for a smaller diameter for the remaining part of the connector extending towards the second electrode, as this will only need to accommodate the second wire. The thinner part for the second electrode will invoke less disturbance in the surrounding tissue during insertion of the connector device, and lowers the risk for subsequent medical complications. Preferably, the second electrode part of the connector is relatively thin, and therefore more suitable to be inserted into the actual organ (for instance the heart) than the relatively thick first electrode part.

Preferably, the sleeve formed by the first electrode is at least partially tapered from a first edge enclosing both the first and second wires, towards a second edge only enclosing the second wire. Thus, the electrically conducting sleeve has a bullet-form which makes it easier to insert the connector into a body when moved into the direction of the taper. The taper also allows for an easy fixation of the second wire that continues through the electrically conducting sleeve.

It is preferred if the shapes of the outer circumference of the edges first electrode element and the electrically insulating sleeve at their joining interfaces are substantially similar. This configuration accomplishes a snug fit and smooth interface, which was found to decrease the risk for damaging tissue while inserting or retracting the connector from a body.

It is preferred if the shape of the outer circumference of the insulating sleeve and the edges of the first electrode element at their joining interface is essentially figure-8 shaped. A figure 8-shaped sleeve provides a very compact outer circumference and allows for a relatively easy accommodation of the first wire and second wire running in a parallel fashion. The compact diameter allows for easy insertion and retraction of the connector.

In a preferred embodiment, the second electrode is formed by an exposed part of said second wire. Such a second electrode is relatively compact, and may be prepared in a relatively simple way by at least partially stripping the isolating sleeve from the second wire. The second wire may be deformed at the exposed part, for instance to a curved form, hook, zigzag pattern or an 'O' shape. Such shapes allow for exposure of the second electrode surface to a smaller surface compared to a straight wire, which enables a more precise delivery of the electric signal to a predetermined spot on the organ.

It is preferred if the connector comprises at least one barbed structure for fixing at least one of the electrodes to the organ. A barbed structure allows for a more reliable fixation of the electrodes to predetermined locations. Preferably, the barbed structure is located relatively close to at least one of the electrodes, for instance within 2 cm from an electrode as measured along the length of the connector. Preferably, the barbed structure is directed in one direction along the length of the connector. This allows for proper fixation in the direction of the barbs, whereas moving the connector into the direction opposite to the barbs is relatively unhampered. Most preferably, the barbed structure is collapsible, which implies that after overcoming a certain threshold force the barbs collapse and the connector may be relatively easily removed. This may be achieved by making at least part of the barbed structure from a resilient material.

Preferably, the barb structure is located at a distance from the first electrode, wherein the second electrode is located between the first electrode element and the barb structure. If the first electrode is relatively thick, it will be fixed under a bias by surrounding tissue; hence the second electrode is reliably fixed between the first electrode and the barb structure which act as anchors.

It is preferred if the barbed structure is formed from partially detached parts of the insulating sleeve, which expose the second wire to form the second electrode. This allows for a relatively easy way to produce a barbed structure and efficient use of available material. The insulating material of the sleeve is usually resilient, and therefore also very suitable for preparing a collapsible barbed structure.

In a preferred embodiment, the second wire extends at least 3 mm beyond said barbed structure, preferably at least 5 mm and most preferably at least 7 mm. This extension allows for the attachment of further functional extensions to the distal end of the second wire.

Preferably a needle is connected to the part of said second wire extending from the first electrode. The needle may be a hollow needle which makes it easier to insert the connector in this direction, or a hook which allows for temporary attachment of this distal end and prevents retraction in a predetermined direction of the connector. The needle is preferably releasable from the connector, which allows for easy removal. It is most convent if the needle for insertion has a maximal diameter at least equal to or larger than the diameter of the insulating sleeve.

The invention also provides a package comprising an electrical connector according to any of the preceding claims, wherein the first and second wires are wound around a spool, and wherein at least the distal ends of the electrical connector are releasably coupled to the spool. This allows for an easy storage and unwinding of the connector from the spool for further processing such as the insertion of the connector into a body. Preferably, the connector is provided with a needle, wherein the needle is releasably attached to a receiving opening of the spool. In a preferred embodiment, the package also contains adaptor means for connecting the connector device to an electrical device, in particular a cardiac device.

The invention further provides a method for removing an electrical connector according to the invention which is temporarily fixed to an organ of a human or animal body, in particular a heart, comprising the steps of: detaching the fixed electrical connector from the organ, and pulling the electrical connector from the body. Due to the smooth surface of the connector according to the invention, the damage to body tissue during retraction is relatively low, and lowers the risk for subsequent medical complications.

BRIEF DESCRIPTION OF THE DRAWINGS

The invention will now be further explained using the following non-limiting embodiments.

FIG. 1 describes a device according to the invention.
FIG. 2 shows details of a device according to the invention.

DETAILED DESCRIPTION OF EMBODIMENTS

Figure 3:
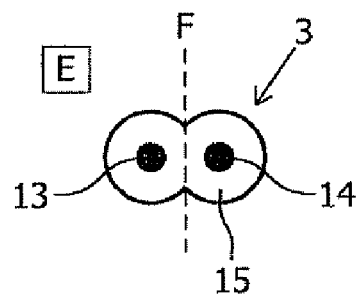
FIGS. 3 and 4 show cross-sections of a device according to the invention.

FIG. 1 describes a connector device 1 according to the invention. A first distal end 2 of an electrically conducting bipolar wire 3 is provided with a thorax needle 4, which may be used to pull the wire 3 through the abdominal wall of a treated person or animal. The thorax needle 4 is a hollow needle enclosing the distal end 2 of the wire. The thorax needle is preferably provided with a snap-off or pull-off construction, which allows easy removal of the needle after the device has been successfully applied to the body of a patient. After removal of the thorax needle 4 the electric conducting wires in the bipolar wire may be stripped, for instance using self stripping adapters, which allow to connect the bipolar wire to an electrical device such as a cardiac pacemaker. Alternatively, the electrically conducting wire 3 may also be a monowire or a quadrupolar wire instead of a bipolar wire.

The second distal end 5 of the bipolar wire 3 is provided with a heart needle 6 for attachment of introducing the distal end 5 into the heart (or another organ). Optionally, the heart needle 6 may be replaced by other suitable attaching means for attachment of the device to the heart. The heart needle is used during the placement of the device; once the device is in the appropriate position, the heart needle 6 is removed, for instance by cutting.

Figure 6:
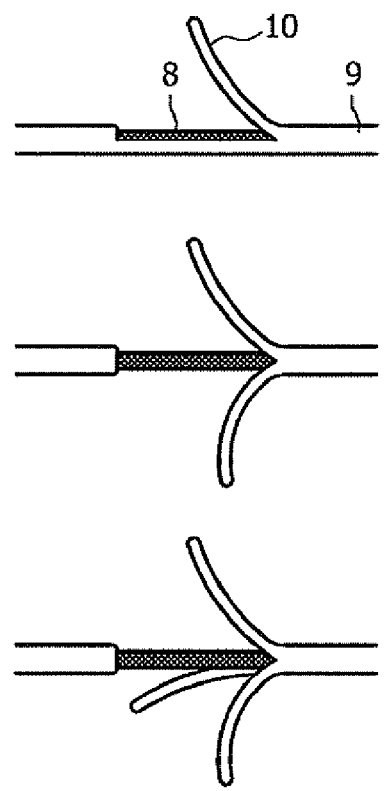
FIG. 6 shows a method of preparing a barbed structure and electrode according to the invention.

The second distal end is also provided with a first electrode 7 and a second electrode 8. The first electrode 7 is an electrically conducting bullet-shaped sleeve made out of metal, preferably medical grade stainless steel, which is electrically connected to one of the wires in the bipolar wire 3. A second wire 9 from the bipolar wire 3 passes through the bullet-shaped sleeve 7 towards the second electrode 8. The second electrode 8 is a stripped portion of the wire 9. By stripping the resilient plastic material of the electrically insulating layer of the wire 9, a barbed structure 10 having 3 or more resilient barbs is formed at the same time, which is illustrated in FIG. 6. The interface 11 between the bipolar wire 3 and the bullet-shaped electrode sleeve 7, as well as the interface 12 between the single wire 9 and the tapered end of the electrode sleeve 7, are substantially smooth, and have a low risk of damaging tissue while being introduced or retracted from a body.

FIG. 2 shows further details of the distal end 5 of the connector device 1 shown in FIG. 1, using the same labels. The smooth interfaces between the electrode sleeve 7 and adjacent wire portions 3, 9 is more clearly seen here. The distance A between the first electrode 7 and the second electrode 8 along the wire 9 is approximately 3 mm. The length B of stripped wire 9 forming the second electrode 8 is approximately 4 mm. The distance C from the barbed structure 10 to the heart needle 6 is approximately 50 mm. The final end of the wire 9 is fixed inside the needle 6, and overlaps over a distance D of approximately 4 mm in order to ensure a proper fixation.

FIG. 3 shows the perpendicular cross section of the wire 3 along line E in FIG. 1. The wire 3 embeds a first electrically conducting wire 13 and a second electrically conducting wire 14, jointly embedded in a sleeve 15 of a flexible electrically insulating material. The first and second electrically conducting wires 13, 14 are connected to the first and second electrodes 7, 8 respectively. The wires 13, 14 may be split into separate wires 13, 14 along the indicated line F, which may be convenient at the distal end 2 at the needle for applying adaptors to connect to an electrical device for generating electric signals such as a cardiac pacemaker.

Figure 4:
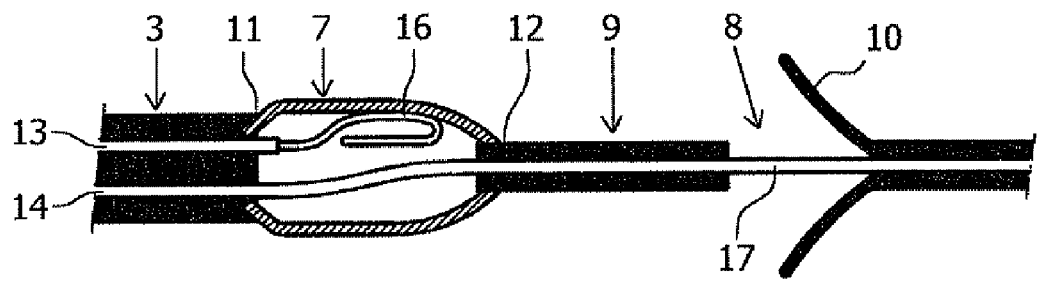

FIG. 4 shows a longitudinal cross section of the first electrode 7, which is formed as an electrically conducting hollow sleeve. A first electrically conducting wire 13 has a stripped section 16 at its distal end, which is in electrical contact with the sleeve 7. The second electrically conducting wire 14 remains electrically insulated within the sleeve and extends on the other end of the sleeve electrode 7 and continues as a single wire 9. The single wire 9 is stripped to reveal the electrically conducting core 17 which forms the second electrode 8. The edges 11, 12 have been pressed in to the resilient insulating material of the wires in order to provide smooth interfaces 11, 12.

Figure 5:
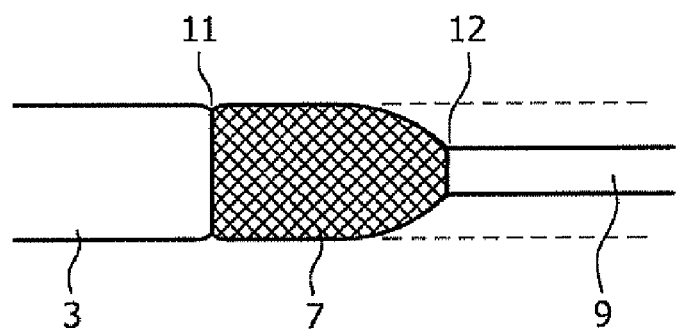
FIG. 5 shows an alternative embodiment of a device according to the invention.

In the alternative embodiment shown in FIG. 5, rather than pressing the edges of the bullet-shaped electrode sleeve 7 into the insulating material of the wires, the diameter of the edges 11, 12 was constructed to match the diameter and shape of the adjoining wires 3, 9. This significantly reduces damage if the connector is inserted or retracted from tissue. The diameter and shape of the edges 11, 12 of the electrically conducting sleeve 7 may also be smaller than the diameter of the wire.

FIG. 6 shows a simple but effective method to provide an electrode surface 8 as well as a resilient barb structure from a wire 9 by selectively stripping insulating material from the wire in three resilient barbs 10. The stripping may be done by regular cutting means, and the barbs 10 are preferably of a roughly even shape by cutting approximately even amounts of insulating material in strips evenly divided along the circumference. Instead of 3 barbs 10, the barbed structure may also be made having 2 barbs or more than 3 barbs, but the 3 barbs were found to be the most convenient to produce and give an appropriate fixation of the electrode 8.

Figure 7:
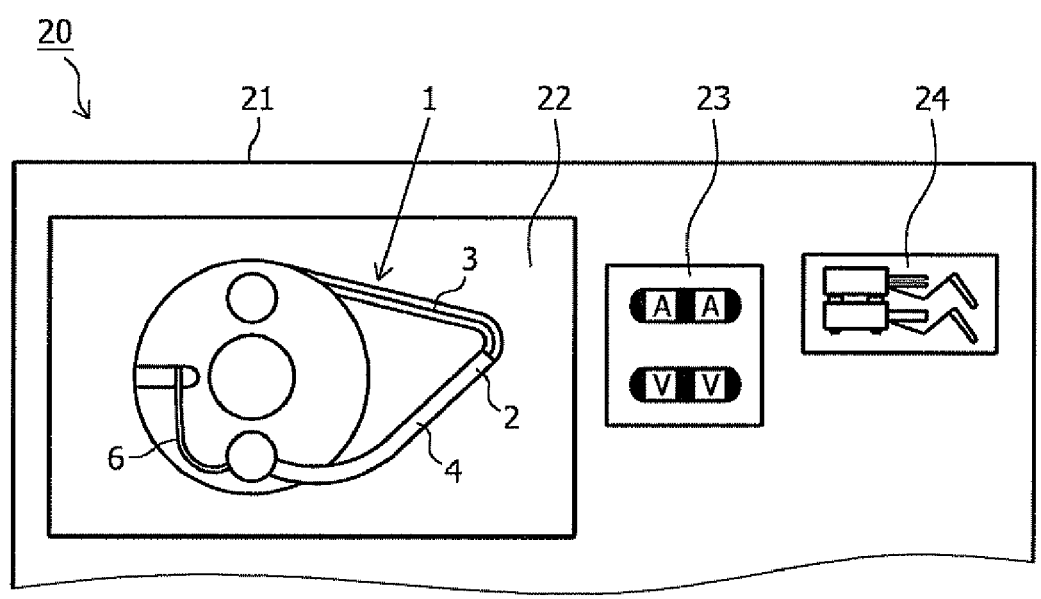
FIG. 7 shows a package including a device according to the invention.

FIG. 7 shows a sealed package 20 in a sterilized clear polymer bag 21, and includes a connector 1 according to the invention as shown in FIG. 1 wound on a spool 22. The package 20 further includes indicating means 23 which may be attached to a split distal end 2 of the wire 3, as well as self stripping adapters 24 which are attached to the split distal end 2 after snapping off the thorax needle 4, in order to connect to an electrical signal generator e.g. a pacemaker.

The invention claimed is:

1. Electrical connector for conveying an electrical signal from a device, in particular a cardiac device, to an organ of a human or animal body, in particular a heart, comprising:
   at least a first electrically conducting wire and a second electrically conducting wire,
   wherein the wires are jointed together in an electrically insulating sleeve,
   a first electrode, which is electrically connected to the first wire, and,
   a second electrode, which is electrically connected to the second wire;
   wherein the first and second electrodes are constructed to deliver an electrical signal at the organ;
   wherein the first electrode forms an electrically conducting sleeve around a conducting part of the first wire and around a non-conducting part of the second wire;
   wherein at least the edges of the electrically conducting sleeve formed by the first electrode are at least partially embedded in the electrically insulating sleeve.

2. Electrical connector according to claim 1, wherein said first electrode is substantially manufactured from an electrical conducting and resilient material.

3. Electrical connector according to claim 1, wherein the second wire extends through the electrically conducting sleeve formed by the first electrode towards the second electrode.

4. Electrical connector according to claim 1, wherein the electrically conducting sleeve formed by the first electrode is connected to a distal end of the first wire located inside the electrically conducting sleeve.

5. Electrical connector according to claim 1, wherein the sleeve formed by the first electrode is at least partially tapered from a first edge enclosing both the first and second wires, towards a second edge only enclosing the second wire.

6. Electrical connector according to claim 1, wherein an outer circumference of the first electrode element and the electrically insulating sleeve at their joining interfaces are substantially similar in shape.

7. Electrical connector according to claim 1, wherein a shape of the outer circumference of the insulating sleeve and the edges of the first electrode element at their joining interface is essentially figure-8 shaped.

8. Electrical connector according to claim 1, wherein said second electrode is formed by an exposed part of said second wire.

9. Electrical connector according to claim 1, wherein the device comprises a barb structure for fixing at least one of the electrodes to the organ.

10. Electrical connector according to claim 9, wherein the barb structure is located at a distance from the first electrode, wherein the second electrode is located between the first electrode element and the barb structure.

11. Electrical connector according to claim 9, wherein the barb structure is formed from partially detached parts of the isolating sleeve, which expose the second wire to form the second electrode.

12. Electrical connector according to claim 11, wherein said second wire extends at least 3 mm beyond said barb structure, preferably at least 5 mm and most preferably at least 7 mm.

13. Electrical connector according to claim 1, wherein a needle is connected to the part of said second core extending from said second edge of said first electrode element.

14. A package comprising an electrical connector according to claim 1, wherein the first and second wires are wound around a spool, and wherein at least the distal ends of the electrical connector are releasably coupled to the spool.

15. A method for removing an electrical connector according to claim 1 fixed to an organ of a human or animal body, in particular a heart, comprising the steps of:

detaching the fixed electrical connector from the organ, and pulling the electrical connector from the body.

* * * * *